United States Patent [19]

Miller

[11] Patent Number: 4,467,350

[45] Date of Patent: * Aug. 21, 1984

[54] METHOD AND APPARATUS FOR RAPIDLY EXTRACTING SIGNIFICANT DATA FROM A SPARSE OBJECT

[75] Inventor: John W. V. Miller, Toledo, Ohio

[73] Assignee: Owens-Illinois, Inc., Toledo, Ohio

[ * ] Notice: The portion of the term of this patent subsequent to Mar. 29, 2000 has been disclaimed.

[21] Appl. No.: 205,054

[22] Filed: Nov. 7, 1980

[51] Int. Cl.³ .............................................. H04N 7/18
[52] U.S. Cl. ................................ 358/106; 250/223 B; 250/563; 356/237; 356/240
[58] Field of Search ...................... 358/106, 107, 101; 250/562, 563, 572, 223 B; 356/237, 238, 240, 430, 431, 434; 209/526, 528; 364/200 MS File, 900 MS File, 515

[56] References Cited

U.S. PATENT DOCUMENTS

| | | | |
|---|---|---|---|
| 4,042,960 | 8/1977 | Wooding, Jr. | 358/101 |
| 4,277,803 | 7/1981 | Sano | 358/106 |
| 4,292,672 | 9/1981 | Southgate | 358/106 |
| 4,323,990 | 4/1982 | Goode et al. | 364/200 |
| 4,378,494 | 3/1983 | Miller | 250/563 |
| 4,378,495 | 3/1983 | Miller | 250/563 |

OTHER PUBLICATIONS

Baba et al., Pin Hole Detector for Mirror Finish Surface Using 1 TV Camera, Nec. Res. & Dev., (Japan), #51, Oct. 1978, pp. 11-15.

Primary Examiner—Joseph A. Orsino, Jr.
Attorney, Agent, or Firm—Gerald T. Welch; Myron E. Click

[57] ABSTRACT

A control circuit for an apparatus for inspecting objects, such as glass bottles and the like, for defects includes an interface circuit connected between a source of data signals and means for processing information obtained from the object. The interface circuit receives the data signals, typically in digital series form, and includes a latch for storing one of the digital signals, a pair of adders, and a storage means for a plurality of threshold signals. Each data signal is compared to the preceding data signal stored in the latch in one of the adders to generate a difference signal representing the difference in magnitudes between the two signals. Each difference signal is compared with a selected one of the stored threshold signals in the other adder to generate an event signal representing the difference in magnitudes between the two signals. The means for processing information includes a pair of control units and a master control means for alternately connecting the control units to the interface means, whereby one of the control units is receiving a group of the event signals representing one object while the other control unit is processing a preceding group of the event signals.

14 Claims, 2 Drawing Figures

METHOD AND APPARATUS FOR RAPIDLY EXTRACTING SIGNIFICANT DATA FROM A SPARSE OBJECT

BACKGROUND OF THE INVENTION

1. Field of the Invention

The present invention relates in general to sidewall inspection devices for containers and in particular to a method and apparatus for extracting significant data with respect to defects from a sparse object, such as a glass bottle.

2. Description of the Prior Art

The use of optical scanning devices for inspecting the sidewalls of containers is well known. Numerous devices, such as those shown in U.S. Pat. Nos. 3,708,680 and 3,716,136, have circuitry including means for receiving and interpreting light passed through or directed onto an item under inspection. Such devices incorporate either a visual display for comparison of the item or employ a device capable of producing a resistance proportional to the intensity of light directed thereon. Whether the output of such a device is visual or electrical in nature, it is eventually compared against a model to determine if the item under inspection is suitable as to size and construction and is without flaws, cracks, or foreign objects. Such devices are each intended to provide an automated inspection means for checking, as in a moving column of bottles, single or multiple objects in that moving column.

U.S. Pat. No. 3,877,821 discloses an apparatus having a scanning array that is serially interrogated to generate a train of pulses having amplitudes representing the light transmitted through an object under inspection. Adjacent pulses are compared to generate pulses having amplitudes which represent the difference in pulse amplitudes. The difference pulses can be utilized to indicate a defect in the object being inspected. U.S. Pat. No. 3,942,001 discloses an apparatus for detecting the presence of extraneous matter or cracks in translucent containers. A spot beam of light is projected through the container to generate an inspection signal which is compared with an acceptance signal. The acceptance signal amplitude is varied in accordance with the position of the spot beam with respect to the container.

SUMMARY OF THE INVENTION

The present invention concerns an apparatus for extracting only the significant data from an optical inspection of a sparse object, such as a glass bottle. A digitized video signal representing a point of inspection is generated by a camera and associated light source to an interface circuit including an adder and a latch in which is stored the digitized video signal from the previous point of inspection. A signal representing the difference between the present digitized signal and the stored digitized signal from the latch is generated by the adder and compared with a stored threshold level for the current point of inspection. If the threshold level is exceeded, an event signal is generated and stored in the interface circuit.

After the object has been scanned, the group of event signals is processed to determine if a defect is present. A master control unit means alternately connects a pair of control units to the interface, whereby one of the control units is receiving a group of event signals while the other control unit is processing a preceding group of event signals.

It is an object of the present invention to provide a means and apparatus for rapidly extracting significant data from a sparse object, such as a glass bottle.

It is another object of the present invention to rapidly extract significant data in a manner suitable for computer analysis.

It is a further object of the present invention to provide a sidewall inspection device that can be easily integrated with an existing apparatus for moving transparent or translucent items past an inspection point, automating the inspection process thereof.

DETAILED DESCRIPTION OF THE PREFERRED EMBODIMENT

Figure 1:
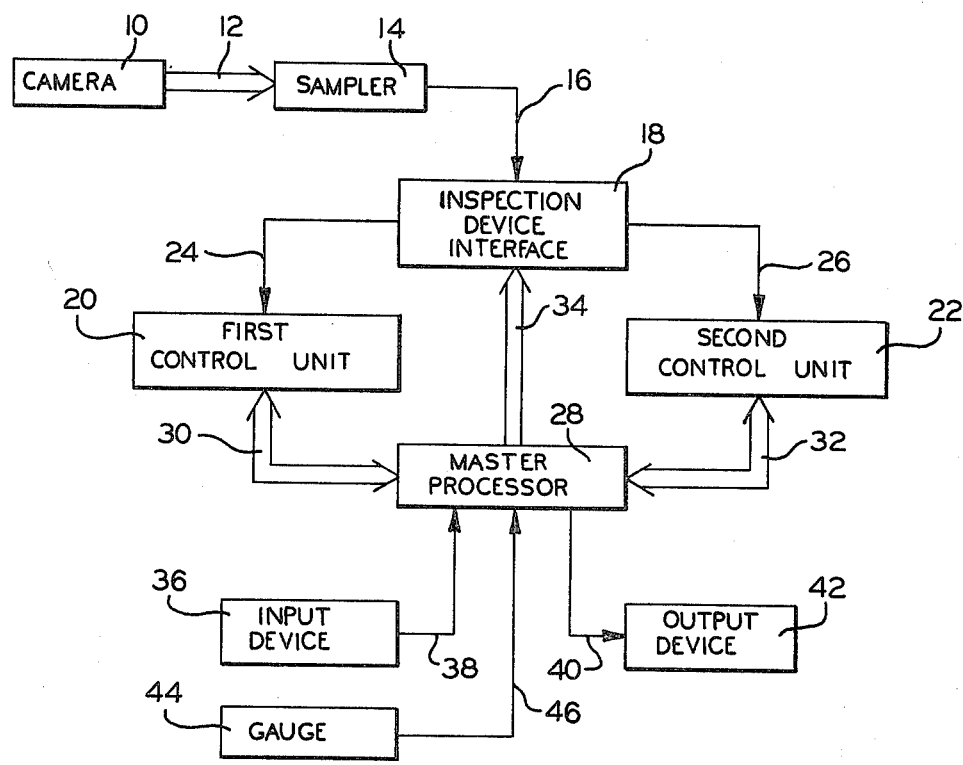
FIG. 1 is a block diagram of an apparatus for detecting defects in objects according to the present invention.

Referring now to the drawings, there is illustrated in FIG. 1 a block diagram of an apparatus for detecting defects in objects according to the present invention. An object, such as a glass bottle (not shown), is scanned by a camera 10. The camera 10 generates a plurality of signals proportional in magnitude to the amount of light received from the glass bottle. In the preferred embodiment of the invention, a light source (not shown) directs a beam of light through the glass bottle under inspection and into the camera 10. The camera 10 includes a plurality of photosensitive devices, such as photodiodes, which are vertically arranged in a linear array. It has been found that a linear array of two hundred fifty-six photodiodes yields statisfactory results. The photodiode is a variable resistance device that will pass a voltage proportional to the amount of light falling thereon. Each photodiode receives light which has passed through different segments or portions of the bottle under inspection. If a flaw, crack, or foreign object is contained in the bottle, then the light passing through that portion of the bottle will be partially blocked or reflected and the corresponding photodiode will register a lesser intensity of light than had no defect been present.

The signals from the photodiodes of the camera 10 are supplied to a sampler 14 on a plurality of lines 12. Each of the photodiodes is sampled in sequential order, producing a series of pixel signals on a line 16 which represent the amount of light which passed through the bottle under inspection along one vertical sequential sweep of the photodiodes. The sampler 14 is a device well known in the art. By rotating the bottle under inspection relative to the camera 10, a plurality of different sweeps can be made, each sweep inspecting a different portion of the bottle. It has been found that about three hundred seventy-five to four hundred sweeps will sufficiently cover an average bottle and insure an accurate inspection. Thus, the sampler 14 generates a plurality of series of pixel signals on line 16 representing the amount of light passing through the inspected portions of the entire bottle.

The pixel signals from the sampler 14 on line 16 are an input to an inspection device interface 18. The interface 18 rapidly extracts significant data from a sparse object, such as a glass bottle, in a manner suitable for computer analysis. When a bottle is ready to be scanned, the interface 18 is enabled to receive and store data concerning that bottle. When no bottle is ready to be scanned, the interface 18 stores the data concerning the last scanned bottle until a new bottle is ready to be scanned. The operation of the interface 18 is more fully explained below.

The interface 18 is a means for generating groups of signals representing the characteristics of the bottle under inspection. The output of the interface 18 is fed to a control circuit for generating a reject signal whenever a defective bottle is detected. The control circuit includes a first control unit means 20 and a second control unit means 22, which receive the output signals from the interface 18 over lines 24 and 26 respectively. The first control unit 20 and the second control unit 22 are each responsive to the groups of signals representing the characteristics of the bottles under inspection for determining whether to generate a reject signal.

The first control unit 20 and the second control unit 22 are connected to a master control unit means or processor 28 by lines 30 and 32 respectively. The master processor 28 also provides inputs to the interface 18 over a plurality of lines 34 to allow an operator to set certain tolerance limits, as will be more fully described below. The master processor 28 alternately connects one of the first and second control units 20 and 22 to the interface 18 to receive groups of signals representing the characteristics of a bottle while the other of the first and second control units 20 and 22 determines whether to generate a reject signal based upon the plurality of signals representing the characteristics of a preceding bottle. Thus, while the first control unit 20 is reading data from the inspection interface 18 concerning a bottle which has just been scanned, the second control unit 22 is processing data obtained on a prior scan to determine whether to generate a reject signal for the preceding bottle.

The master processor 28, the first control unit 20, and the second control unit 22 can all be microprocessors, such as a model 6800 manufactured by Motorola which is conventional and well known in the art. The master processor 28 has an input device 36 by which an operator can program the system and set various tolerance parameters. The input device 36 is connected to the master processor 28 by a line 38. The master processor 28 is also connected by a line 40 to an output device 42, such as a video display, so as to permit an operator to monitor or calibrate the system. Alternatively, the device 42 can be a means responsive to a reject signal generated by the master processor 28 for rejecting a particular bottle which has been determined to be defective. A further input to the master processor 28 is a gauge 44. The gauge 44 is provided to generate a signal on a line 46 when a bottle is in the proper position to be scanned.

The interface 18 can receive data so long as the gauge 44 signals that a bottle is in the proper scanning position. When the gauge 44 ceases to generate such a signal, as during the period when the inspected bottle is removed and an uninspected bottle is moved in, the collected information is stored in the interface 18. The master processor 28 prevents interference between the first and second control units 20 and 22 by selecting one of the units to receive the data held in the interface 18. When all of the data has been transferred to the first control unit 20, for example, the interface 18 is free to receive new data on the next bottle as soon as the signal from the gauge 44 is restored. The first control unit 20 processes the data in order to determine whether to generate a reject signal. When scanning is completed on the next bottle and the gauge 44 ceases to generate its signal, the accumulated data is stored in the interface 18. The master processor 28 then selects the second control unit 22 to receive the data while the first control unit 20 continues to process the original information. Thus, each of the control units 20 and 22 has two full cycles of the gauge 44 to process the data concerning each bottle to determine whether or not to generate a reject signal. By providing parallel processing paths, the control circuit increases the speed and efficiency of the inspection apparatus.

Figure 2:
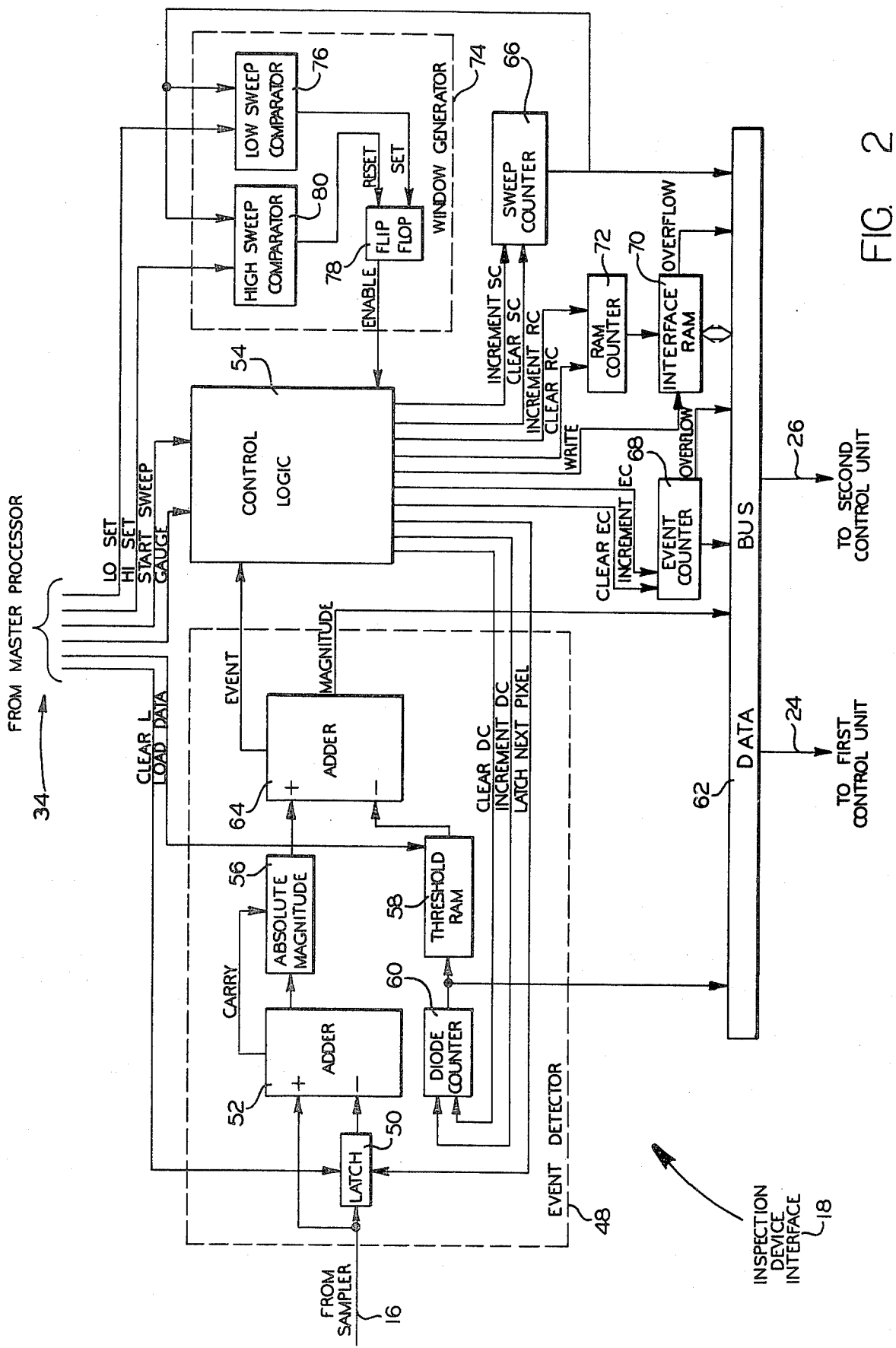
FIG. 2 is a block diagram of the inspection device interface of the apparatus for detecting defects of FIG. 1.

Referring now to FIG. 2, there is illustrated a block diagram of the details of the inspection device interface 18. The interface 18 is a means for rapidly extracting significant data from a sparse object, such as a glass bottle, in a manner suitable for computer analysis. The sampler 14 can generate digital signals, or analog signals to an analog-to-digital converter, representing the magnitude of the light received by the camera 10. Line 16 presents the plurality of signals to an event detector 48 including a data latch 50 and an adder 52. The latch is a means for storing one of the plurality of signals. In the illustrated embodiment, the preceding pixel signal is stored in the latch 50 and is presented to the complementary input of adder 52. Thus, the adder 52 is a means for generating a signal which represents the difference between the magnitude of the stored preceding pixel signal in the latch 50 and the successive pixel signal presented on line 16. The output of the adder 52 is a signal representing the difference in the magnitudes of adjacent pixel signals. When the difference signal is generated by adder 52, the present pixel signal is stored in latch 50 to be compared with the next pixel signal. A control logic unit 54 of the interface 18 generates a command over a LATCH NEXT PIXEL line to cause the latch 50 to store the present pixel signal available on line 16. The contents of the latch 50 can be cleared to zero by a command from the master processor 28 over a CLEAR L line.

The difference signal from the adder 52 can be either positive or negative, depending upon the magnitudes of the present and previous pixel signals. Because only the magnitude of the difference between adjacent pixel signals is relevant in the detection of defects, it is convenient to feed the difference signal to a means for generating the absolute magnitude of the difference signal. As illustrated, the output from adder 52 is fed to an absolute magnitude circuit 56. The circuit 56 can be constructed of a plurality of exclusive OR gates, as is well known in the art. The CARRY output of adder 52 controls the absolute magnitude circuit 56 such that the output is always positive. Rectification of the difference signal prevents misleading comparison readings in the event detector 48.

The event detector 48 includes a means for storing a threshold signal. In the preferred embodiment, a threshold random access memory (RAM) 58 is provided for storing a plurality of threshold signals. Each threshold signal stored in the threshold RAM 58 corresponds to a specific pixel difference signal generated by the adder 52. The means for selecting the individual threshold signal from the threshold RAM 58 which corresponds to the present difference signal is a diode counter 60. The diode counter 60 can be cleared to zero by a command from the control logic 54 over a CLEAR DC line and can be incremented by a command over an INCREMENT DC line. The diode counter 60 provides the threshold RAM 58 with the memory address of the proper threshold signal. The desired threshold signals can be loaded into the threshold RAM 58 from the master processor 28 over a LOAD DATA line. The output of the diode counter 60 is also connected to an internal data bus 62.

The signal from the threshold RAM 58 is presented to the complementary input of an adder 64 where it is combined with the signal from the absolute magnitude circuit 56. The adder 64 is a means for generating event signals when the difference signal obtained from the absolute magnitude circuit 56 differs from the threshold signal obtained from the threshold RAM 58. Event signals are generated, over an EVENT line to the control logic 54, indicating the detection of a defect, and over a MAGNITUDE line to the internal data bus 62, indicating by how much the difference signal differed from the threshold signal.

Upon receiving a signal from the gauge 44 that a bottle is ready to be scanned, the master processor 28 generates a signal over a GAUGE line to the control logic 54. In response to that signal, the control logic 54 generates a signal over a CLEAR SC line to a sweep counter 66. The contents of the sweep counter 66 are thus cleared to zero before each bottle is scanned. The output of the sweep counter 66 is connected to the internal data bus 62.

To initiate a sweep, the mater processor 28 generates a signal over a START SWEEP line to the control logic 54. In response to that signal, the control logic 54 increments the sweep counter 66 by generating a signal over an INCREMENT SC line. The control logic 54 also clears the contents of the diode counter by generating a signal over the CLEAR DC line. The control logic 54 further generates a signal over a CLEAR EC line to clear an event counter 68. These three initialization functions prepare the interface 18 for the receipt of data. The output of the event counter 68 is connected to the internal data bus 62. The event counter 68 generates a signal on an OVERFLOW line to the data bus 62 when the contents of the register exceed its limits. The event counter 68 is incremented by the control logic 54 over an INCREMENT EC line each time that the event detector 48 signals that an event has occurred.

The interface 18 includes a means for storing the event signals. An interface random access memory (RAM) 70 is provided for reading and storing the signals available on the data bus 62. The first control unit 20 and the second control unit 22 alternatively read the accumulated data from the interface RAM 70 through the data bus 62 and lines 24 and 26 respectively. Data is stored in the interface RAM 70 when the control logic 54 generates a signal over a WRITE line. The interface RAM 70 also generates a signal on an OVERFLOW line to the data bus 62 when the contents of the register exceed its limits. A RAM counter 72 provides the interface RAM 70 with memory address locations. The RAM counter 72 can be cleared to zero by a command from the control logic 54 over a CLEAR RC line and can be incremented by the control logic 54 by a command over an INCREMENT RC line.

The interface 18 also includes a means for defining a range for extracting data. In the illustrated embodiment, a window generator 74 is provided to limit the number of sweeps over which data can be extracted. A lower sweep limit is entered by an operator through the input device 36 to the master processor 28. The instruction is sent over a LO SET line to a low sweep comparator 76. The output of the sweep counter 66 is also an input to the low sweep comparator 76. When the number in the sweep counter 66 equals or exceeds the number generated over the LO SET line, the low sweep comparator 76 generates a signal over a SET line to a flip-flop 78. The flip-flop 78 generates a signal over an ENABLE line to the control logic 54, instructing it to process the incoming data. Signals received by the interface 18 on sweeps taken of a bottle below the lower sweep limit are ignored to prevent erroneous data associated with the initial sweeps from being processed. Similarly, the operator can enter a high sweep limit value to cause the interface 18 to stop processing data after a certain number of sweeps. The master processor 28 sends the instruction over a HI SET line to a high sweep comparator 80. The output of the sweep counter 66 is also an input to the high sweep comparator 80. When the number in the sweep counter 66 equals or exceeds the number generated over the HI SET line, the high sweep comparator 80 generates a signal over a RESET line to the flip-flop 78. The flip-flop 78 thus ceases to generate the signal over the ENABLE line, causing the control logic 54 to ignore all subsequent data.

Prior to utilizing the apparatus for detecting defects, the operator will enter the parameters under which the machine will operate through the input device 36. The parameters include the low and high sweep limits and the group of threshold signals. The low and high sweep limits define the sweep window, which is the range of sweeps over which data can be accepted by the interface 18. By selecting a particular set of threshold signals to be loaded into the threshold RAM 58, the operator determines the acceptable tolerances of light deviation which will cause an event to be detected. The master processor 28 loads the appropriate data into the interface 18.

When a bottle has been moved into a proper position for scanning, the gauge 44 generates a signal to the master processor 28. The signal is relayed along the GAUGE line to the control logic 54, which generates signals to clear the contents of both the sweep counter 66 and the RAM counter 72. These tasks are performed each time a new bottle is ready to be inspected. The interface 18 is then prepared to receive data from the camera 10.

At the beginning of each sweep, the master processor 28 generates a signal over the START SWEEP line to the control logic 54. The control logic 54 generates appropriate signals to clear the contents of the diode counter 60, clear the contents of the event counter 68, and increment the contents of the sweep counter 66. These tasks are performed at the beginning of each sweep made by the sampler 14.

The incoming pixel signals are fed to the adder 52 and the latch 50. The latch 50 holds the previous pixel signal at its output, which is then fed to the complementary input of the adder 52. Thus, the output of the adder 52 represents the difference between the two adjacent pixel signals. The output of the adder 52 is fed to the absolute magnitude circuit 56, which insures that the input to adder 64 is always a positive signal.

The threshold RAM 58 holds the programmed plurality of threshold signals, each of which corresponds to a specific difference signal representing a pair of pixels. Since each pixel signal represents a sampled photodiode in the camera 10, the diode counter 60 can be incremented with each incoming pixel signal to select the memory address of the appropriate threshold signal stored in the threshold RAM 58. That particular threshold signal is fed to the complementary input of adder 64 to be compared with the actual difference signal generated by adder 52 and rectified by the absolute magnitude circuit 56. The output of adder 64 is a plurality of event signals which represent a comparison between the difference signal and the threshold signal. When the magnitude of the difference signal exceeds a predetermined amount, the adder 64 will generate an event signal over the EVENT line to the control logic 54. The magnitude of the event signal as well as the output of the diode counter are gated onto the data bus 62 for storage in the interface RAM 70.

When an event is detected during the sweep window, as defined by the operator using the window generator 74, the control logic 54 generates signals which increment the event counter 68 and increment the RAM counter 72. The control logic 54 also generates a signal over the WRITE line to the interface RAM 70 to read and store the contents of the diode counter 60 and the magnitude of the output adder 64. This process is repeated with each pair of adjacent pixel signals until a sweep is completed. The signal on the START SWEEP line is removed at the end of each sweep, causing the contents of the sweep counter 66 and the event counter 68 to be written into the interface RAM 70 if one or more events have occurred in that particular sweep. Thus, in each sweep where an event is detected, the gathered data includes a series of events denoted by diode number and event magnitude, followed by a final single entry consisting of the sweep number and the number of events which occurred in that sweep. When the next sweep of the same bottle begins, the contents of the diode counter 60 are cleared to zero, the contents of the event counter 68 are cleared to zero, and the sweep counter 66 is again incremented. The scanning continues until the window generator 74 disables the interface 18 when the high sweep limit has been reached.

The groups of signals stored in the interface RAM 70 which represent the characteristics of the inspected bottle are then fed to either the first control unit 20 or the second control unit 22, as determined by the master processor 28. The data in the interface RAM 70 is downloaded into the selected control unit, which determines whether or not to generate a reject signal for that particular bottle. Two checks are made before processing begins to make sure that the interface 18 has not overflowed because of an unusually bad bottle. These checks are indicated by status flags on the event counter 68 and the interface RAM 70. If the contents of either unit exceeds the capability of the register, a signal is generated over the resepctive OVERFLOW lines. When either overflow signal is present, the bottle will be immediately rejected because of a gross defect.

As stated above, the format of the data which is read by the selected control unit includes a series of diode numbers and associated event magnitudes, followed by a sweep number and a number of events. The bottle data is downloaded from the interface RAM 70 to the particular control unit. By checking each event along a sweep to see if it can be linked to a preceding event, the control units 20 or 22 can generate a string. A string is defined as a collection of one or more events in proximity to each other and having four properties which are calculated during generation. These properties include: the beginning of the string, which is the first diode number; the end of the string, which is the last diode number; the magnitude of each string, which is the sum of the magnitudes of each event comprising the string; and the number of events that formed the string. Checking for excess string magnitude occurs during string generation and the decision process will halt if a string magnitude exceeds a user-adjustable threshold. In other words, the selected control unit 20 or 22 links together events within a single sweep to determine if the sum of the magnitudes of the events exceeds a user-specified tolerance. If so, a reject signal is generated and the particular bottle will be removed.

If string checking does not reject the bottle, another processing stage is entered wherein the strings are checked to see if they form blobs. A blob is defined as collection of strings in proximity to each other. The string diode numbers must overlap, or at most be within a user-specified range, for the end of one string on one sweep and the beginning of another string on a different sweep. A blob has three properties which are calculated during formation. These properties include blob width, blob magnitude, and the number of events in the blob. During blob formation, blob width and blob magnitude are checked against user-specified tolerances and processing stops if either threshold is exceeded. If a bottle is not rejected because of blob width or blob magnitude, the number of events contained in the blob is compared to another user-specified number. If the number of events exceeds the specified tolerance, the bottle will also be rejected. If the bottle has not been rejected for any of the above reasons, it is considered a good bottle and no reject signal will be generated.

The apparatus for detecting defects can also be utilized to generate and display a picture of the object under inspection. A bottle is inspected under the normal procedure described above and data is stored in the interface RAM 70. When the bottle has been completely scanned, the master processor 28 instructs either the first control unit 20 or the second control unit 22 to receive the data from the inspection interface 18. The selected control unit 20 or 22 does not process the received information but rather transmits the data in raw form to the master processor 28. The gathered data includes the diode number, the sweep number, and the event magnitude for each event detected by the interface 18. The data is then presented to the output device 42, which can include a two-dimensional graphic module and a video screen. The graphic module and video screen are well known in the art. The data can be displayed in a two-dimensional graphic form, utilizing the sweep number of each event as the horizontal component and the diode number of each event as the vertical component. The video screen will display a dot at each sweep and diode number location where an event was detected. The result is a two-dimensional representation of the inspected bottle showing all of the detected defects, as if the bottle had been cut through one side and unwrapped for display. The event magnitude may be used in conjunction with a synthetic threshold level which can be varied to generate new pictures which show the effect that different threshold levels have. Using the apparatus in this mode, an operator is aided in determining what the appropriate threshold levels for the particular style of bottle should be. Although the preferred embodiment of the invention provides only a two-dimensional representation of the object under inspection, it will be appreciated that a three-dimensional representation could be generated on the video screen by the use of additional circuitry. Such circuitry is also well known in the art.

The apparatus for detecting defects can also be utilized to monitor the video output of the line scan camera. Such a use permits an operator to calibrate the interface 18 without requiring the use of an oscilloscope. When the apparatus is operated in this mode, the master processor 28 continuously clears the contents of the latch 50 to zero by generating a signal over the CLEAR L line. With the latch 50 cleared, the plurality of pixel signals on lines 16 from the sampler 14 pass through the adder 52 unaltered. The master processor 28 also utilizes the LOAD DATA line to load the threshold RAM 58 with all zeros. Thus, every pixel signal is detected as an event and is stored in the interface RAM 70. Since the interface RAM 70 is limited in size, only one sweep of the bottle is taken to prevent memory overflow. The master processor 28 selects either the first control unit 20 or the second control unit 22 to receive the data from the interface RAM 70. The data includes the diode number and event magnitude for each pixel of the sweep. The data is transferred from the selected control unit 20 or 22 to the master processor 28. The master processor 28 relays the information to the output device 42, which again can consist of a two-dimensional graphic module and a video screen. The graphic module can utilize the diode number as the horizontal component and the event magnitude as the vertical component. The graph which is thus displayed on the video screen represents the amount of light received by the photodiodes over a single sweep. The procedure can be repeated continuously to simulate an oscilloscope. However, unlike an oscilloscope, no sweep or gain adjustments are necessary since the data is always properly scaled to a specific diode number or event magnitude. Operation of the apparatus in this mode permits an operator to make sensitivity adjustments relating to the event magnitude voltage without requiring the use of an oscilloscope.

In accordance with the provisions of the patent statutes, the principle and mode of operation of the invention have been explained and illustrated in its preferred embodiment. However, it must be understood that the invention may be practiced otherwise than as specifically illustrated and described without departing from its spirit or scope.

What is claimed is:

1. In an apparatus for detecting defects in successive objects and for providing a plurality of digital signals each representing the magnitude of light received from a corresponding point on an object, an interface circuit comprising:
   means for storing the digital signals;
   means for generating for each one of the digital signals a difference signal representing the difference in magnitudes between said one digital signal and a preceding one of the digital signals;
   means for storing a plurality of different threshold signals, each associated with the location of a different corresponding point on the object; and
   means for comparing each of said difference signals with each of said threshold signals at corresponding points on the object and generating an event signal when the magnitude of said difference signal differs from the magnitude of said corresponding threshold signal.

2. The interface circuit according to claim 1 wherein said means for storing said event signal includes a random access memory.

3. The interface circuit according to claim 1 further comprising means for storing the event signal.

4. The interface circuit according to claim 1 or 3 wherein said means for generating said difference signal includes means for generating said difference signal as the absolute magnitude of said difference signal.

5. The interface circuit according to claim 1 or 3 wherein said means for storing the digital signals includes a latch for storing said preceding one of the digital signals.

6. The interface circuit according to claim 1 or 3 wherein said means for generating said difference signal includes an adder having one input connected to the source of digital signals and a complementary input connected to an output of said means for storing the digital signals for generating said difference signal.

7. The interface circuit according to claim 1 or 3 wherein said means for comparing includes an adder having one input connected to an output of said means for generating said difference signal and a complementary input connected to an output of said means for storing a plurality of threshold signals for generating said event signal.

8. The interface circuit according to claim 1 or 3 wherein said means for storing a plurality of threshold signals includes a random access memory.

9. The interface circuit according to claim 8 including means for selecting one of said threshold signals associated with the location of a corresponding point on the object.

10. A method of inspecting successive objects for defects by processing a plurality of digital signals, each representing the magnitude of light received from a corresponding point on an object, comprising the steps of:
   (a) storing a plurality of different threshold signals each associated with the location of a different corresponding point on the object;
   (b) generating for each one of the digital signals a difference signal representing the difference in magnitudes between said one digital signal and a preceding one of the digital signals;
   (c) comparing each of said difference signals with each of said threshold signals at corresponding points on the object and generating an event signal when the magnitude of said difference signal differs from the magnitude of said corresponding signal; and
   (d) storing said event signals.

11. The method according to claim 10 including a step of storing each of the digital signals as said preceding one until said difference signal is generated.

12. The method according to claim 10 wherein said step (b) includes generating said difference signals as the absolute magnitude of said difference signals.

13. The method according to claim 10 wherein said step (b) is performed by combining said one digital signal and said preceding one of the digital signals in an adder.

14. The method according to claim 10 wherein said step (c) is performed by combining said difference signal and said corresponding threshold signal in an adder.

* * * * *